United States Patent [19]

Welker

[11] Patent Number: 4,882,939

[45] Date of Patent: Nov. 28, 1989

[54] PURGE VALVE

[75] Inventor: Brian H. Welker, Sugar Land, Tex.

[73] Assignee: Welker Engineering Company, Sugar Land, Tex.

[21] Appl. No.: 243,261

[22] Filed: Sep. 12, 1988

[51] Int. Cl.$^4$ .............................................. G01N 1/10
[52] U.S. Cl. .............................. 73/864.03; 73/864.62;
137/454.5; 137/454.6; 251/291
[58] Field of Search ........................ 73/864.62, 864.63;
137/384, 454.2, 454.4, 454.5, 454.6; 251/291

[56] References Cited

U.S. PATENT DOCUMENTS

| | | | |
|---|---|---|---|
| 3,040,770 | 6/1962 | Boettcher et al. | 137/454.6 |
| 3,550,625 | 12/1970 | Adams, Jr. | 137/454.5 X |
| 3,892,130 | 7/1975 | Winget et al. | 73/864.62 |
| 4,172,670 | 10/1979 | Welker | 73/864.62 X |
| 4,403,519 | 9/1983 | Welker | 73/864.62 |
| 4,459,865 | 7/1984 | Welker | 73/864.62 |
| 4,463,603 | 8/1984 | Welker | 73/864.62 X |
| 4,463,804 | 8/1984 | Rodney et al. | 73/864.63 X |
| 4,628,750 | 12/1986 | Welker | 73/864.62 X |
| 4,829,835 | 5/1989 | Welker | 73/864.2 X |

Primary Examiner—Tom Noland
Attorney, Agent, or Firm—Gunn, Lee & Miller

[57] ABSTRACT

The purge valve assembly is designed for use with a constant pressure sample cylinder for purging of the cylinder prior to installation in the field for collection of spot and composite samples. The purge valve assembly can be installed in newly manufactured constant pressure sample cylinders or can be added as an after market item. The purge valve assembly consists of a retainer which compresses a sealing element into engagement with an end cap to prevent fluid from bypassing the retainer. A valve element is urged into engagement with the sealing element by a spring thus closing the valve and preventing the escape of any fluid from the sample cylinder. To open the valve a valve actuator is manually depressed thus dislodging the valve element from sealing engagement with the sealing member thus allowing fluid to be vented to atmosphere or purged. An alternative embodiment combines the valve element and valve activator into an integral element. In another embodiment two sealing elements are used instead of one.

24 Claims, 3 Drawing Sheets

FIG.1
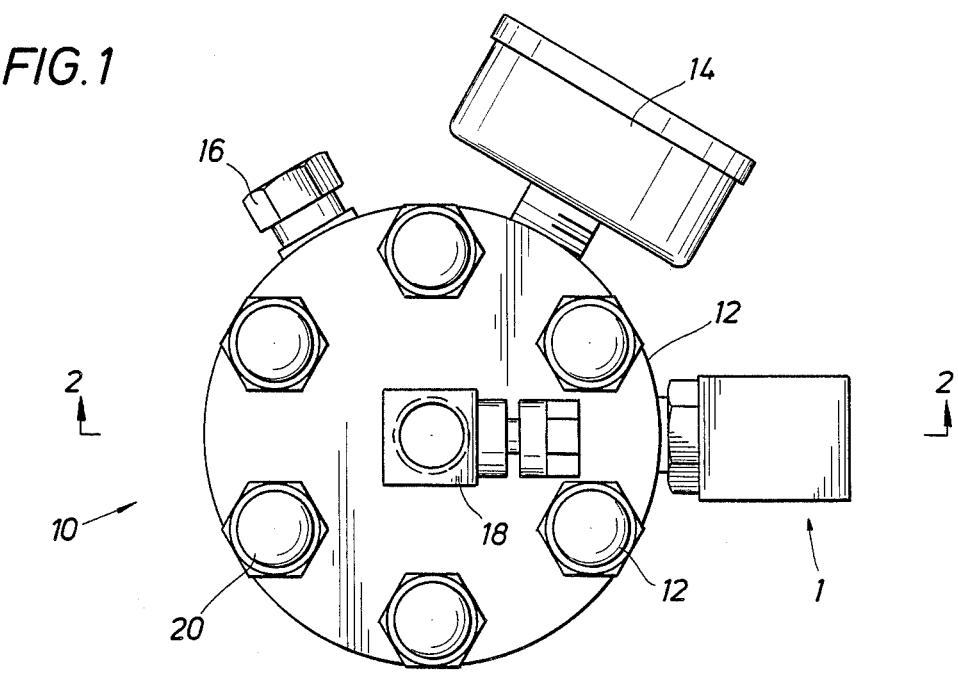
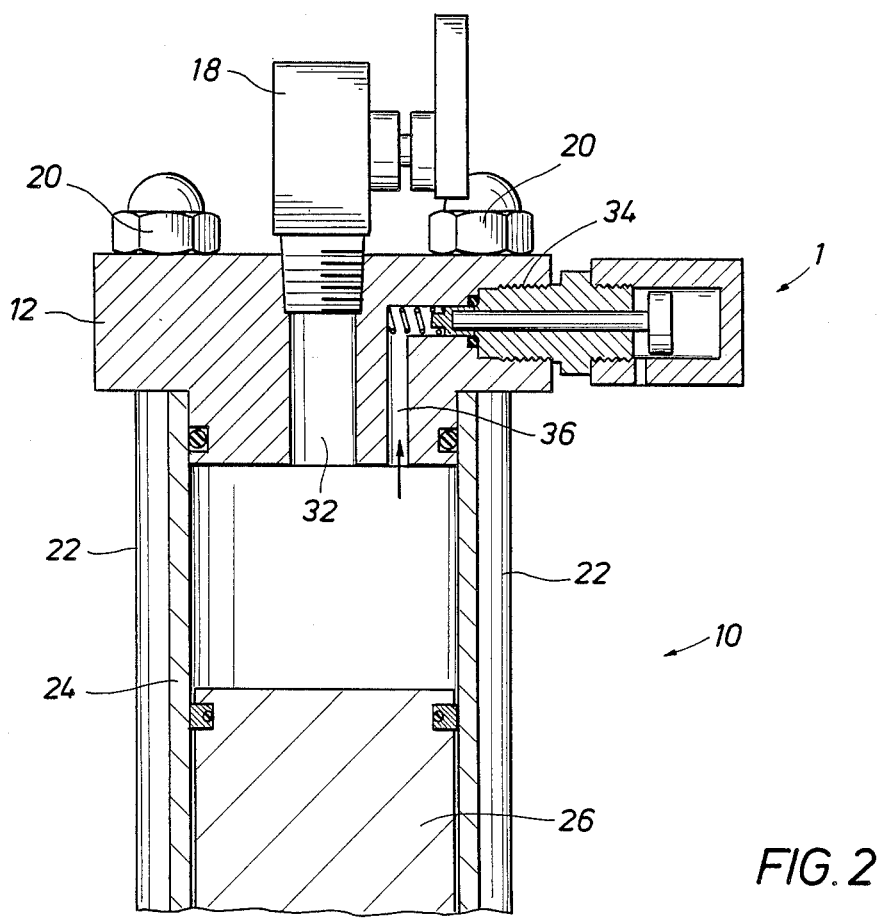
FIG.2

PURGE VALVE

RELATED APPLICATION

This application relates to copending application Ser. No. 07/243,589 filed on Sept. 12, 1988 entitled "Constant Pressure Sample Cylinder with Spheroid Mixer" filed by applicant.

BACKGROUND OF THE INVENTION

1. Field of Invention

This invention relates to a valve mechanism which can be used as a purge valve for constant pressure sample cylinders.

2. Description of the Prior Art

Constant pressure sample cylinders are used worldwide to collect samples of various hydrocarbons. The construction and design of constant pressure sample cylinders is well known to those skilled in the art and is disclosed in patent application Ser. No. 07/243,589 filed on Sept. 12, 1988 and in prior U.S. Pat. Nos. 4,628,750; 4,463,599; 4,459,865; 4,403,519; and 4,172,670 assigned to Welker Engineering Company which are incorporated herein by reference. Constant pressure sample cylinders are manufactured by Welker Engineering Company and others.

In a typical constant pressure sample cylinder, a first end cap will be positioned on one end of the cylinder and a second end cap on the other end. The end caps are typically held in place by a plurality of elongate stud bolts which usually run the length of the cylinder and are joined by nuts on either end of the bolts. Inside the cylinder is a slidable piston which divides the cylinder into a first chamber for storage of sample and a second chamber referred to as the precharge chamber. The sample chamber communicates with a passageway in the first end cap. A sample inlet valve is connected to this first passageway to control sample flow. The precharge chamber communicates with a passageway in the second end cap. A precharge valve is connected to this second passageway to control flow of precharge fluid.

Prior to being taken to the field, cylinders are "precharged" in the laboratory. The precharge is usually equal to or slightly greater than expected pressures in the sample environment. For example, if pipeline pressure is approximately 500 psi, the second chamber will be pressurized to approximately 500 psi. This precharge moves the piston into contact with the first end cap and thereby effectively eliminating or reducing the volume in the sample chamber. There will always be a slight void between the piston and first end cap prior to collection of sample. As sample is collected the piston moves back against the precharge.

In a typical situation the constant pressure sample cylinder will be taken to an oil well for sampling of production. After the sample has been collected in the cylinder, it will be taken from the field to a laboratory for analysis. Crude oil is typically analyzed for numerous factors including but not limited to viscosity, specific density, sulfur content, etc.

Constant pressure sample cylinders are also used to a somewhat lesser degree to collect gaseous hydrocarbons such as natural gas. As will be known to those skilled in the art, natural gas at the wellhead typically contains methane, propane, butane, isobutane, natural gasoline and/or ethane. In certain conditions, such as production from a wet well, several of the constituents of natural gas may condense to form what is known as "light liquids" in the industry. When taking a natural gas sample, it is important that the liquids and gases remain in a steady state which is representative of the production from the well. A steady state means that the existing liquids do not vaporize and the existing vapors do not liquefy. Constant pressure sample cylinders have proven their usefulness for keeping natural gas samples in a steady state both during collection in the field and during transport from the field to a laboratory for analysis.

Traditionally natural gas was priced primarily by volume; however in more recent years the BTU content has become another important pricing consideration. The best way to accurately analyze the BTU content is to take a representative sample in the field and to make sure that the sample stays in a steady state during collection and delivery to the laboratory.

Calorimeters were initially used by laboratories for BTU analysis of a natural gas sample. Samples were typically collected in five gallon sample cylinders which were sometimes referred to as "bombs" by those in the industry. These types of cylinders do not contain an internal piston like the constant pressure sample cylinder. In order for the calorimeter to make an analysis of the BTU content of a sample it must burn for approximately fifteen minutes or more and will typically utilize ten to fifty cubic feet of natural gas from the sample cylinder. The calorimeter uses relatively large volumes of gas to operate and therefore older type sample cylinders needed to collect a relatively large volume of sample.

Most modern laboratories and pipelines now use gas chromatographs for analyzing the contents of natural gas. The BTU content is then calculated based on the content analysis from the gas chromatograph. Gas chromatographs may use one tenth of a milliliter or less of natural gas for purposes of analysis. It is therefore no longer necessary to collect large volume samples due to the improvement in the art of testing.

It has therefore become much more critical that the sample be as representative of the whole or possible. Any contaminant in the sample cylinder or in the sample itself could adversely affect the BTU analysis which dramatically affects the price of the natural gas.

It has therefore become common practice to purge a sample container prior to making a sample in the field. The purpose of purging the sample container is to eliminate any air which might be present in voids or passageways connecting to the sample container or in the sample container itself. Without an effective purge the collection of an accurate sample is virtually impossible.

Air shows up in a gas chromatograph primarily as nitrogen. Any excess amount of air trapped in passageways or voids and analyzed as nitrogen by the gas chromatograph could adversely affect the BTU analysis of the sample. It has therefore been recognized by those skilled in the art that any air trapped in passageways or in the sample container itself will adversely affect the representativeness of the sample. Prior to the invention of the present purge valve assembly there have been two common techniques for purging a sample container prior to sampling in the field.

The first prior art technique used a tee in connection with a purge valve as discussed hereinafter. Most sample stations in natural gas pipelines contain one or more valved outlets connected to probes in the pipeline. The initial step in the purging process is to open the valve connected to such a probe to verify open communication with the pipeline. When the natural gas is vented to atmosphere in this fashion the operator is certain that the probe is not plugged. Opening a valve in this manner will also disburse any light liquids which may be entrapped in the probe or the valve. The valve is then piped to a tee having a purge valve on one side of the T and the inlet valve to the constant pressure sample cylinder on the other side. The inlet valve on the sample side of the constant pressure sample cylinder is opened, the purge valve at the tee is closed and the valve at the pipeline is opened. This allows pipeline pressure which is typically in excess of 500 psi to reach through the connective tubing, through the tee, through the inlet valve on the cylinder, through the passageways in the end cap on the constant pressure sample cylinder and into the sample chamber in direct contact with the piston. Although this circuit is pressurized with pipeline pressure, there is no true fluid flow because there is no outlet from the sample chamber. The piston does not move in this situation because the precharge side of the constant pressure sample cylinder has been prepressurized to equal or exceed pipeline pressure.

The next step in this type of purging process is to close the valve on the pipeline and open the purge valve at the tee. This vents the pipeline pressure in the connective tubing and the cylinder to atmosphere; again there is no true flow because it is a closed circuit. This purging process is then repeated three to five times to hopefully eliminate all air from the connective tubing, the inlet valve on the sample cylinder, the passageways in the end cap and the void between the piston and the end cap in the sample cylinder. Because the piston has been driven into contact with the end cap the void between the piston and the end cap is practically diminimus; however, when dealing with gases, very small areas could retain enough air or other contaminants to adversely affect the sample. At lower pipeline pressures of fifteen to twenty pounds the purging process should be repeated approximately fifteen to seventeen times. After the purging process is complete, the constant pressure sample cylinder is disconnected from the piping and connected to a sampler for collection of a sample.

This old technique of purging has a significant disadvantage because the purge valve is connected to a tee which is located between the pipeline and the constant pressure sample cylinder. There is therefore no direct flow through the inlet valve on the constant pressure sample cylinder or the passageways in the end cap or the void formed between the piston and the end cap. This lack of direct flow was recognized by Applicant as a significant disadvantage which needed to be corrected in order to improve sampling techniques.

Applicant therefore developed a second prior art technique using a purge valve in a different location. Applicant began to drill additional passageways in the end cap of its constant pressure sample cylinder and install hardface valves in these passageways. This repositioned valve provided an outlet to the circuit to create a true flow when purging. Typical valves used by the Applicant for this purpose include Whitey valve model no. SS-20KM4F4 and Manifold Fabricators valve model no. MNV-MF-25-316S. This outlet connected to the sample chamber made a significant improvement in the purging process by allowing gases to actually flow through the inlet valve, the passageways in the end cap and the void between the piston and the end cap.

This improved purging process requires that the inlet valve to the constant pressure sample cylinder be connected to the pipeline; however there is no need for an intermediate tee or a purge valve at the tee. The purge valve is directly attached to the end cap. In this improved purging process the inlet valve to the constant pressure sample cylinder would be opened allowing pipeline pressure to reach through the inlet valve, the passageways in the end cap and into the void between the piston and the end cap. The inlet valve would then be closed and the purge valve would be opened thus venting the fluids to atmosphere. The purge valve would then be closed and the inlet valve would be opened. Repetition of the aforementioned steps in this improved purging process actually allows natural gas to pass from the pipeline through the inlet valve, the passageways in the end cap, the void between the piston and the end cap and out through the purge valve to atmosphere. This improved purging method virtually eliminated any air from the sample.

Unfortunately because of the added cost for an additional hardfaced purging valve this improved purging process has not been widely adopted by industry. In order to promote greater sampling accuracy and encourage use of this improved purging technique applicant has invented a low cost purge valve which can be directly installed in the end cap and used in lieu of prior hard face purge valves which were relatively much more expensive.

SUMMARY OF THE INVENTION

The present invention is a purge valve assembly for use with constant pressure sample cylinders. The purge valve assembly can be installed as an after market item in constant pressure sample cylinders which have previously been sold or the purge valve assembly can be installed in newly manufactured constant pressure sample cylinders. The purge valve assembly is mounted in the sample end cap and connects to the sample chamber by a passageway through the end cap. The purge valve assembly is used to vent to atmosphere, natural gas or another purging fluid from the sample inlet valve, the passageways in the sample end cap, and the void between the piston and the sample end cap. The purge valve is used prior to the collection of a sample in the field.

The purge valve assembly has a sealing element which is compressed between a valve seat and a retainer. A spring urges a valve member into sealing engagement with the sealing element when the valve is closed. The purge valve assembly is normally closed thus preventing the escape of any sample to atmosphere. When the purge valve assembly is opened, a valve actuator unseats the valve member and allows a purging fluid to flow through the purge valve assembly to atmosphere. One unique feature of this invention is a valve actuator which can be removed from the purge valve assembly once it is installed in the field to prevent inadvertent release of sample.

BRIEF DESCRIPTION OF DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodimetts.

FIG. 1 is a perspective view of the purge valve assembly mounted on the sample end cap of a constant pressure sample cylinder.

FIG. 2 is a section view taken along line 2—2 of FIG. 1 showing the purge valve assembly, and a portion of a constant pressure sample cylinder.

DESCRIPTION OF THE PREFERRED EMBODIMENT

Figure 3:
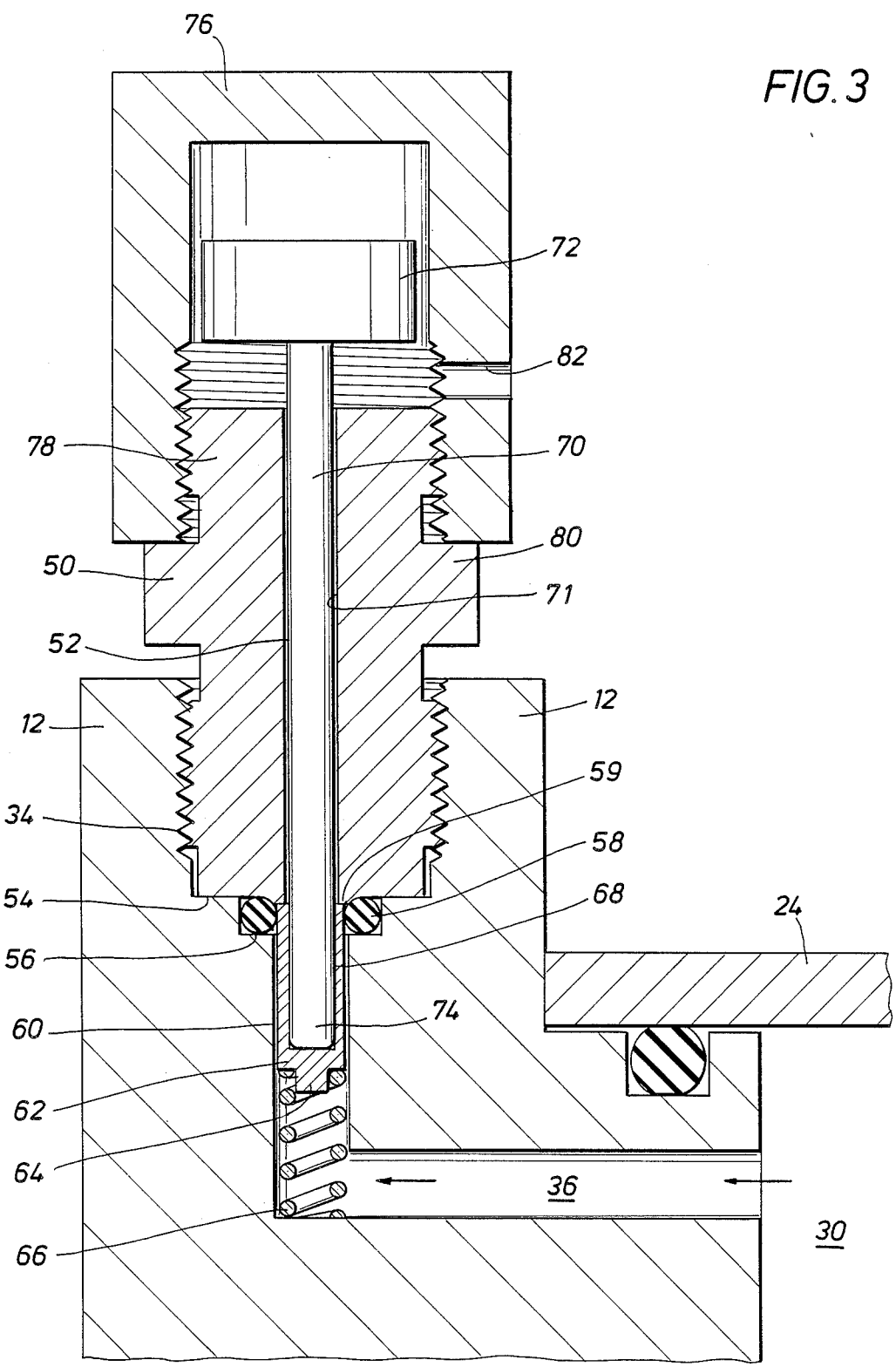
FIG. 3 is an enlarged section view of the purge valve assembly mounted in the sample end cap as shown in FIG. 2.

In FIG. 1, the purge valve assembly is generally identified by the numeral 1. The constant pressure sample cylinder is generally identified by the numeral 10. The sample end cap 12 also supports a pressure gauge 14, a bursting relief assembly 16 and a sample inlet valve 18. The pressure gauge measures the pressure in the sample chamber. The bursting relief assembly prevent rupture of the cylinder in the event of overpressure. The sample end cap 12 is held in place by a plurality of nuts 20 which engage a plurality of stud bolts 22 better seen in FIG. 2.

In FIG. 2, the sample end of the constant pressure sample cylinder 10 is shown in section view. The cylinder 24 engages the sample end cap 12 on one end and the precharge end cap on the other end. The precharge end cap is not shown in FIG. 2 but is similar in configuration to the end cap 12 except there is no purge valve in the precharge end cap. Both end caps are sealed to the cylinder 24 by O-rings. The stud bolts 22 pass through the sample end cap 12 and the precharge end cap and are secured by a plurality of nuts 20. The piston 26 divides the constant pressure sample cylinder 10 into a sample chamber 30 and a precharge chamber not shown in the drawing.

Prior to the filling of the sample chamber 30 the piston 26 will be urged into contact with the sample end cap 12 by the pressure in the precharge chamber. The surfaces of the piston 26 and the end cap 12 are not lapped and therefore there will always be a slight void between the two members when they are touching one another.

In order for a sample to be stored in sample chamber 30 it first passes through the sample inlet valve 18 the inlet passage 32 in the inlet cap 12 and thereafter into the sample chamber 30. In FIG. 2 the piston 26 has moved away from the sample end cap 12 thus indicating that sample has been stored in the sample chamber. The purge valve assembly 1 is mounted in the sample end cap 12 in a port 34. The port 34 is in open communication with a passageway 36. The passageway 36 is in open communication with the sample chamber 30. If the purge valve assembly were not in place, fluid could flow from sample chamber 30 through the passageway 36 and the port 34 to atmosphere.

In FIG. 3 the purge valve assembly 1 is shown in enlarged cross-sectional view. The sample end cap 12 acts as a valve body for the purge valve assembly 1. A port 34 is formed in the sample end cap 12. A flow passageway 36 is also formed in the sample end cap 12. The sample chamber 30 is in open communication with the flow passageway 36 and the port 34 when the purge valve assembly is removed.

The port 34 is threaded to receive a retainer 50 which has a central longitudinal bore 52 passing through the center of the retainer 50. The port 34 has a first shoulder 54 and a second shoulder 56 therein. The second shoulder 56 acts as a valve seat to receive the elastomeric O-ring 58. The O-ring 58 is compressed between the retainer 50 and the valve seat 56 to establish a seal between the retainer 50 and the sample end cap 12. The O-ring 58 is further held in place by a small shoulder 59 which extends from the retainer 50. The shoulder 59 prevents the O-ring from being sucked up into the bore 52 when the valve opens.

The port 34 narrows to circular opening 60 below the first shoulder 54 and the second shoulder 56. A valve member 62 is positioned in the opening 60. The valve member 62 is a cylindrical plug having a generally cylindrical protrusion 64 extending from one end thereof. The cylindrical protrusion 64 engages a spring 66. The valve element 62 contains a cylindrical depression 68 in the end opposite to the cylindrical protrusion 64. The cylindrical depression 68 is sized to conform and receive a valve actuator 70 which can also be referred to as a valve stem.

The valve actuator 70 is sized to fit in the bore 52 of the retainer 50. The annulus 71 between the retainer 50 and the activator 70 is sufficient to allow the passage of liquids from the sample chamber 30. The actuator 70 has a disc shaped button mounted on one end and a nose 74 on the other end which engages the cylindrical depression 68 of the valve element 62. A cap 76 threadably engages the upper neck 78 of the retainer 50. The retainer 50 has an enlarged shoulder area 80 to engage a wrench for tightening the retainer 50 in the sample end cap 12. The cap 76 bottoms on the shoulder 80. The sample end cap 76 has an orifice 82 drilled therein to prevent pressure build up inside the cap 76 in the event of a leak from the sample chamber 30 through the purge valve assembly 1.

The valve actuator 70, also known as a valve stem, is rigidly attached to the disc shaped button 72 thus forming one integral element as shown in FIG. 3. The valve actuator or valve stem 70 is not rigidly attached to the valve element 60. This provides a unique feature to the present invention because the valve actuator 70 can be removed from the purge valve assembly 1 once the purging process has been completed and the sampler has been installed in the field. Removal of the actuator 70 prevents inadvertent release of sample by unskilled or untrained individuals. Removal of the valve actuator 70 provides a foolproof system to prevent unwanted escape of sample in the field, during transit or back at the lab. One suggested application of the present invention is to manufacture the valve actuator 70 from disposable plastic and encourage field operators to dispose of the stem after the constant pressure sample cylinder has been purged and installed in the field for the collection of a sample. This will prevent inadvertent release of sample after it has been collected and will be a positive indicator that the sample cylinder was purged prior to installation. After the sample has been tested by the lab, a new plastic actuator 70 could be installed in the purge valve assembly prior to being sent to the field for reuse.

OPERATION OF THE PREFERRED EMBODIMENT

The purge valve assembly 1 is normally in a closed position preventing any fluid in the sample chamber 30 from escaping to atmosphere. In the closed position the spring 66 urges the valve element 62 into sealing engagement with the O-ring 58. When the valve element 62 engages the O-ring 58, fluid cannot pass through the annulus 71 to atmosphere. The O-ring 58 performs a dual purpose by providing a seal between the retainer 50 and the valve body at the valve seat 56.

To open the purge valve assembly the cap 76 is removed and the button 72 is pushed thus driving the actuator 70 into contact with the valve element 62. Pressure on the actuator 70 is transferred through the valve element 62 and causes the spring 66 to compress. The valve element 62 then moves out of sealing contact with O-ring 58. Fluid is then able to pass from the sample chamber 30 through the passageway 36, up the opening 60 and into the annulus 71 and thereafter to atmosphere. After the venting or purging process has been completed, pressure is released from the button 72 thus releasing the pressure on the spring 66 causing it to urge the valve element 62 back into engagement with the O-ring 58 stopping the flow of pressurized fluid from the sample chamber 30.

Figure 4:
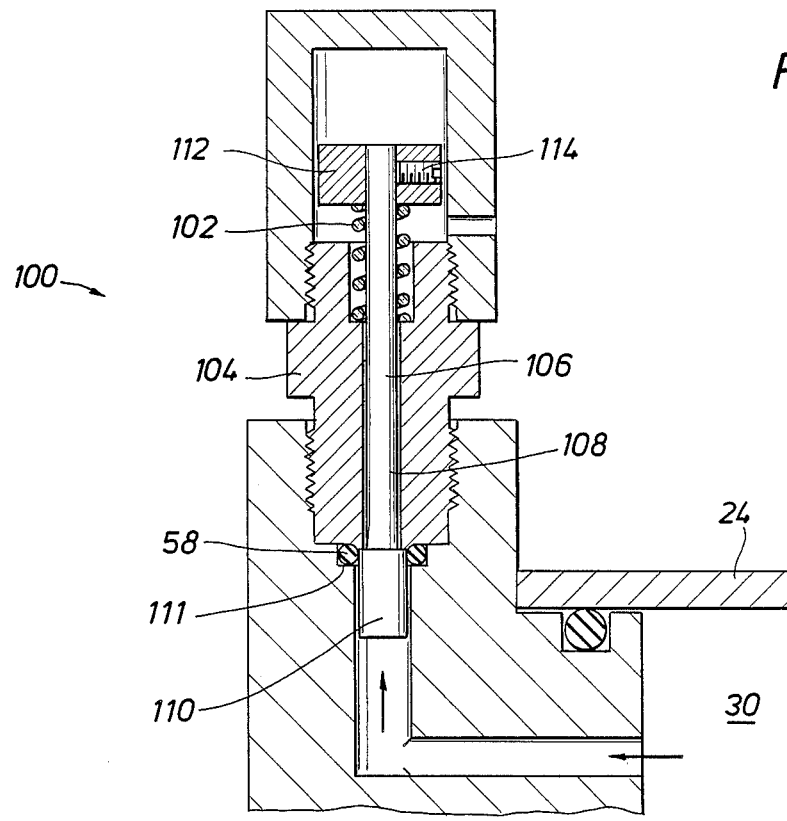
FIG. 4 is a section view of an alternative embodiment of the purge valve assembly showing an integral valve member and valve actuator.

In FIG. 4 an alternative design of the purge valve assembly is shown and is generally identified by the numeral 100. The two primary differences between the purge valve assembly 1 and the purge valve assembly 100 are the location of the spring and the configuration of the valve member and valve actuator. In the alternative embodiment of the purge valve assembly 100, the spring 102 is located in the retainer 104. In the alternative embodiment 100 the valve member and the valve actuator become one integral element 106.

The valve member 106 has an elongate shaft 108 having a cylindrical plug 110 on one end and a disc shaped button 112 on the other end. The cylindrical plug 110 and the shaft 108 are preferably formed from a single piece of metal or plastic and are rigidly attached one to another. The button 112 is removably attached by a locking screw 114 to the shaft 108. The valve member 106 includes the button 112, the shaft 108 and the cylindrical plug 110 as an integral unit. This alternative embodiment does not have a removable valve actuator 70 as shown in FIG. 3.

The operation of the purge valve assembly 100 is very similar to the purge valve assembly 1 except that the spring 102 acts upon the button 112 instead of the valve member 62 as shown in FIG. 3. The cylindrical plug 110 engages the O-ring 58 and forms a seal thus preventing the escape of fluid from the sample chamber 30. The O-ring 58 likewise engages the retainer 104 and the seat 111 to prevent the flow of fluid past the retainer.

Figure 5:
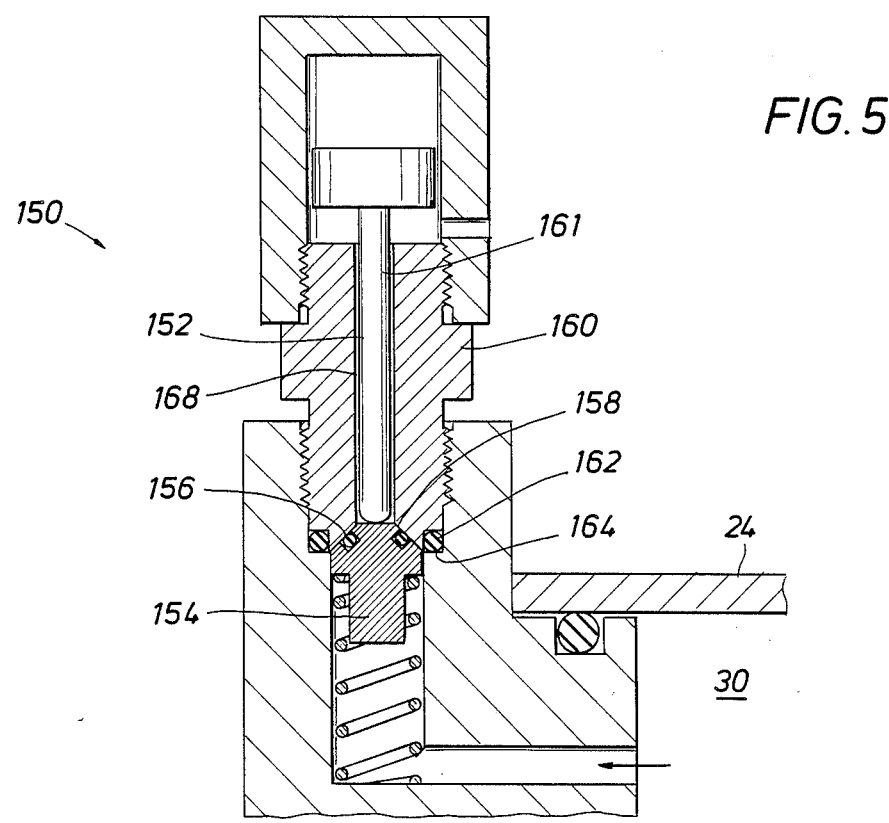
FIG. 5 is a section view of another alternative embodiment of the purge valve assembly.

In FIG. 5 an alternative embodiment of the purge valve assembly is generally identified by the numeral 150. In this alternative embodiment a valve actuator 152 also referred to as a valve stem engages a valve member 154. The valve actuator 152 is not rigidly connected to the valve member 154. The actuator 152 can be removed from the purge valve assembly 150 after the constant pressure sample cylinder has been purged and installed in the field for sampling. In this regard the alternative embodiment shown in FIG. 5 has some of the same operational features and advantages of the embodiment shown in FIG. 3.

The valve member 154 carries an O-ring 156 which engages a shoulder 158 on the lower portion of the retainer 160. The O-ring 156 forms a seal between the valve member 154 and the shoulder 158 of the retainer 160 to prevent fluid from escaping through the annulus 161 to atmosphere. A second O-ring 162 is compressed by the retainer 160 against a valve seat 164 to prevent the flow of fluid past the retainer 160. Both the O-ring 156 and the O-ring 162 are required to perform the same sealing function as the O-ring 58 discussed in the prior embodiments.

The purge valve assembly 150 operates in a manner similar to the purge valve assembly described in FIG. 3 except the sealing function is accomplished by two O-rings instead of one. In FIG. 5 the actuator 152 is depressed thus driving the valve element 154 down against the force of the spring 66 and out of engagement with shoulder 158 thus allowing fluid to pass through the annular area 168 to atmosphere. When pressure is removed from the actuator 152, the spring 66 urges the valve element 154 back into engagement with the shoulder 158 thus creating a seal and preventing further escape of fluid to atmosphere.

While the foregoing is directed to the preferred embodiment of the present invention, other and further embodiments of the invention may be devised without departing from the basic scope thereof, and the scope thereof is determined by the claims which follow.

What is claimed is:

1. A purge valve assembly for use with an elongate constant pressure sample cylinder having a first end cap at one end of the cylinder and a second end cap at the opposite end and a slidable piston positioned inside the cylinder defining a first chamber and a second chamber, the assembly comprising:
   (a) said first end cap of said cylinder forming a port and a passageway to allow fluid communication from said first chamber through said passageway, through said port, through said purge valve assembly and to atmosphere when said purge valve assembly is opened;
   (b) a retainer removably engaging said port in said first end cap, said retainer having a central longitudinal bore in open communication with said port and the atmosphere;
   (c) a valve element;
   (d) a valve stem passing through said longitudinal bore of said retainer and removably engaging said valve element;
   (e) a sealing element held in said port by said retainer, said sealing element establishing sealing engagement with said end cap and said retainer to prevent the escape of said fluid from said port past said retainer to the atmosphere, said sealing element establishing sealing engagement with said valve element to prevent fluid from passing from said port to said bore to said atmosphere when said purge valve assembly is closed; and
   (f) a spring in said port urging said valve element into an engagement with said sealing element to prevent fluid from escaping from said first chamber when said purge valve assembly is closed.

2. The apparatus of claim 1 further including a protective cap positioned on said retainer to shield said valve stem and to prevent the inadvertent opening of said purge valve assembly.

3. The apparatus of claim 2 further including a vent hole in said protective cap.

4. The apparatus of claim 1 wherein said sealing element is an elastomeric O-ring.

5. The apparatus of claim 4 wherein said valve element is a cylindrical plug having a cylindrical protrusion on one end for engagement with said spring and a cylindrical depression in the other end to receive said valve stem.

6. The apparatus of claim 5 wherein said valve stem is an elongate shaft having a disc shaped button mounted on one end, the other end of said shaft engaging said valve element.

7. A purge valve assembly for use with an elongate constant pressure sample cylinder having a first end cap at one end of the cylinder and a second end cap at the opposite end and a slidable piston positioned inside the cylinder defining a first chamber and a second chamber, the assembly comprising:
(a) said first end cap of said cylinder forming a flow passage and defining a circular valve seat about said flow passage;
(b) an elastomeric circular sealing element being received within said valve seat and forming an inner peripheral sealing surface;
(c) a retainer element being secured to said end cap and sufficiently compressing said circular sealing element within said valve seat to establish a seal between said valve body and said retainer element;
(d) a valve member establishing sealing engagement with said inner peripheral sealing surface and being linearly movable from its sealing engagement with said inner peripheral sealing surface to permit the flow of fluid past said circular sealing element and through said flow passage;
(e) means continuously urging said valve member toward its sealing engagement with said inner peripheral sealing surface; and
(f) a valve actuator removably extending from said valve member and being movable for imparting unseating movement to said valve member against the force of said urging means.

8. A purge valve assembly for use with an elongate constant pressure sample cylinder having a first end cap at one end of the cylinder and a second end cap at the opposite end and a slidable piston positioned inside of the cylinder defining a first chamber, and a second chamber the assembly comprising:
(a) said first end cap of said cylinder forming a port and a passageway to allow fluid communication from said first chamber through said passageway, through said port, and through said purge valve assembly to atmosphere when said purge valve assembly is opened;
(b) a retainer removably engaging said port in said first end cap, said retainer having a central longitudinal bore in open communication with said port and the atmosphere;
(c) a valve element;
(d) a sealing element held in said port by said retainer, said sealing element establishing sealing engagement with said end cap and said retainer to prevent the escape of fluid from said port past said retainer to the atmosphere, said valve element establishing sealing engagement with said sealing element to prevent fluid from passing from said port to said bore to the atmosphere when said purge valve assembly is closed; and
(e) a spring in said port urging aid valve element into engagement with said sealing element to prevent said fluid from escaping from said first chamber when said purge valve assembly is closed.

9. The apparatus of claim 8 further including a protective cap positioned on said retainer to prevent the inadvertent opening of said purge valve assembly.

10. The apparatus of claim 8 further including a vent hole in said protective cap.

11. The apparatus of claim 10 wherein said sealing element is an elastomeric O-ring.

12. The apparatus of claim 11 wherein said valve element is an elongate shaft passing through the longitudinal bore of said retainer, said shaft having a disc shaped button on one end and a cylindrical plug on the other end, said plug having a cylindrical protrusion extending therefrom for engagement with said spring, said plug engaging said sealing element.

13. A purge valve assembly for installation in a valve body having a port sized and configured to receive said purge valve assembly, said port being in open communication with a source of pressurized fluid, the assembly comprising:
(a) a retainer removably engaging said port in said body, said retainer having a central longitudinal bore in open communication with said port and atmosphere;
(b) a valve element;
(c) a valve stem passing through said longitudinal bore of said retainer and removably engaging said valve element;
(d) a sealing element held in said port by said retainer, said sealing element establishing sealing engagement with said body and said retainer to prevent the escape of fluid from said port past said retainer to the atmosphere, said valve element establishing sealing engagement with said sealing element to prevent fluid from passing from said port to the atmosphere when said purge valve assembly is closed; and
(e) a spring in said port urging said valve element into engagement with said sealing element to prevent fluid from escaping to the atmosphere when said purge valve assembly is closed.

14. The apparatus of claim 13 further including a protective cap positioned on said retainer to shield said valve stem means and to prevent the inadvertent opening of said purge valve assembly.

15. The apparatus of claim 14 further including a vent hole in said protective cap.

16. The apparatus of claim 13 wherein said sealing element is an elastomeric O-ring.

17. The apparatus of claim 16 wherein said valve element is a cylindrical plug having a cylindrical protrusion on one end for engagement with said spring and a cylindrical depression in the other end to receive said valve stem.

18. The apparatus of claim 17 wherein said valve stem is an elongate shaft having a disc shaped button mounted on one end, the other end of said shaft engaging said valve element.

19. A purge valve assembly comprising:
(a) a valve body forming a flow passage and defining a circular valve seat about said flow passage;

(b) an elastomeric circular sealing element being received within said valve seat and forming an inner peripheral sealing surface;

(c) a retainer element being secured to said valve body and sufficiently compressing said circular sealing element within said valve seat to establish a seal between said valve body and said retainer element;

(d) a valve member establishing sealing engagement with said inner peripheral sealing surface and being linearly movable from its sealing engagement with said inner peripheral sealing surface to permit the flow of fluid past said circular sealing element and through said flow passage;

(e) means continuously urging said valve member toward its sealing engagement with said inner peripheral sealing surface; and (f) a valve actuator removably extending from said valve member and being movable for imparting unseating movement to said valve member against the force of said urging means.

20. A purge valve assembly for installation in a valve body having a port sized and configure to receive said purge valve assembly, said port being in open communication with a source of pressurized fluid, the assembly comprising:

(a) a retainer removably engaging said port in said body, said retainer having a central longitudinal bore in open communication with said port and atmosphere;

(b) a valve element;

(c) a sealing element held in said port by said retainer, said sealing element establishing sealing engagement with said body and said retainer to prevent the escape of fluid from said port past said retainer to the atmosphere, said valve element establishing sealing engagement with said sealing element to prevent fluid from passing from said port to said bore to the atmosphere when said purge valve assembly is closed; and (d) a spring in said port urging said valve element into engagement with said sealing element to prevent fluid from escaping to the atmosphere when said purge valve assembly is closed.

21. The apparatus of claim 20 further including a protective cap positioned on said retainer to prevent inadvertent opening of said purge valve assembly.

22. The apparatus of claim 21 further including a vent hole in said protective cap.

23. The apparatus of claim 20 wherein said sealing element is an elastomeric O-ring.

24. The apparatus of claim 23 wherein said valve element is an elongate shaft passing through the longitudinal bore of said retainer, said shaft having a disc shaped button on one end and a cylindrical plug on the other end, said plug having a cylindrical protrusion extending therefrom for engagement with said spring, said plug engaging said sealing element.

* * * * *